(12) United States Patent
Hedmann et al.

(10) Patent No.: US 11,738,126 B2
(45) Date of Patent: Aug. 29, 2023

(54) CONCENTRATE CONTAINER

(71) Applicant: FRESENIUS MEDICAL CARE DEUTSCHLAND GMBH, Bad Homburg (DE)

(72) Inventors: Frank Hedmann, Volkach (DE); Nadja Schubert, Schweinfurt (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 685 days.

(21) Appl. No.: 16/626,927

(22) PCT Filed: Jun. 27, 2018

(86) PCT No.: PCT/EP2018/067236
§ 371 (c)(1),
(2) Date: Dec. 27, 2019

(87) PCT Pub. No.: WO2019/002361
PCT Pub. Date: Jan. 3, 2019

(65) Prior Publication Data
US 2020/0222610 A1 Jul. 16, 2020

(30) Foreign Application Priority Data
Jun. 28, 2017 (DE) .................. 10 2017 114 400.5

(51) Int. Cl.
*A61M 1/16* (2006.01)
*A61M 1/28* (2006.01)

(52) U.S. Cl.
CPC ............ *A61M 1/1656* (2013.01); *A61M 1/28* (2013.01); *A61M 1/1607* (2014.02);
(Continued)

(58) Field of Classification Search
CPC ...... A61J 1/05; A61J 2205/10; A61M 1/1607; A61M 1/1656; A61M 1/1666;
(Continued)

(56) References Cited

U.S. PATENT DOCUMENTS 5,385,564 A * 1/1995 Slater .................... A61M 1/167
604/82
5,971,972 A * 10/1999 Rosenbaum .............. A61J 1/10
604/411

(Continued)

FOREIGN PATENT DOCUMENTS

DE 102011106248 1/2013
EP 1872814 1/2008

(Continued)

*Primary Examiner* — Dirk R Bass
(74) *Attorney, Agent, or Firm* — Jacobson Holman PLLC

(57) ABSTRACT

The present invention relates to a concentrate container having a concentrate that is configured to form a dialysis solution after its dilution with a diluting agent, in particular with water, wherein the concentrate container is in communication with a first connector having a first code that contains at least one piece of information on the concentrate; and wherein the concentrate container is furthermore in communication with a second connector whose second code differs from the first code, with the second code containing at least one piece of information on the dialysis solution.

14 Claims, 2 Drawing Sheets

Figure 1:
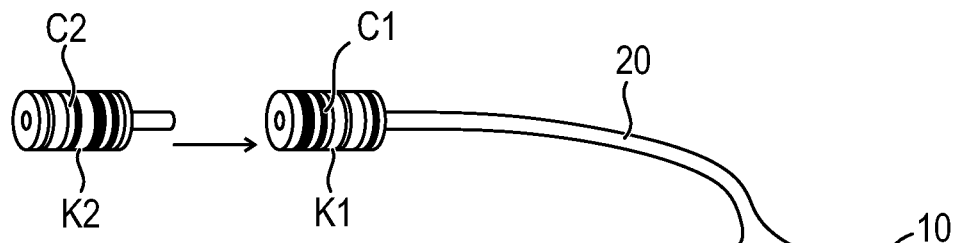

(52) U.S. Cl.
CPC ..... *A61M 2205/12* (2013.01); *A61M 2205/50* (2013.01); *A61M 2205/6072* (2013.01)

(58) Field of Classification Search
CPC ...... A61M 1/1668; A61M 1/167; A61M 1/28; A61M 1/287; A61M 2205/12; A61M 2205/50; A61M 2205/6018; A61M 2205/6063; A61M 2205/6072
See application file for complete search history.

(56) References Cited

U.S. PATENT DOCUMENTS

| | | | |
|---|---|---|---|
| 6,468,424 B1 * | 10/2002 | Donig | A61M 1/1668 210/321.71 |
| 2008/0015493 A1 * | 1/2008 | Childers | A61M 1/3458 604/29 |
| 2012/0123322 A1 * | 5/2012 | Scarpaci | A61M 1/28 250/573 |

FOREIGN PATENT DOCUMENTS

| | | |
|---|---|---|
| EP | 2167163 | 3/2010 |
| EP | 2258419 | 12/2010 |

\* cited by examiner

CONCENTRATE CONTAINER

The present invention relates to a concentrate container having a concentrate that is designed to form a dialysis solution after its dilution with a diluting agent, in particular with water.

It is customary in peritoneal dialysis to administer ready-made dialysis solutions. They are typically administered in volumes of 3 to 6 liters. 3 bags a day are required in a typical peritoneal dialysis treatment, which means a substantial logistical effort and substantial storage space.

It is the underlying object of the present invention to provide a concentrate container that makes possible a simple solution preparation with small storage requirements.

This object is achieved by in accordance with the invention by a concentrate container having a concentrate that is configured to form a dialysis solution after its dilution with a diluting agent, in particular with water, characterized in that the concentrate container is in communication with a first connector having a first code that contains at least one piece of information on the concentrate; and in that the concentrate container is furthermore in communication with a second connector whose second code differs from the first code, with the second code containing at least one piece of information on the dialysis solution.

Provision is accordingly made that the concentrate container is in communication with a first connector having a first code that contains at least one piece of information with respect to the concentrate and that the concentrate container is furthermore in communication with a second connector whose second code differs from the first code, wherein the second code contains at least one piece of information with respect to the dialysis solution.

Such a concentrate container requires substantially less volume than a container filled with a completed dialysis solution. The concentrate can be diluted with a diluting agent on site, i.e. at the POC (point of care) such as at home so that a dialysis solution is produced from the concentrate. It is pointed out at this point that both a solution ready to be administered and a solution that may have to be further diluted or mixed to obtain the completed dialysis solution are to be understood under the term "dialysis solution".

The first connector has a first code and the second connector has a second code differing therefrom. The first code contains at least one piece of information relating to the concentrate such as the quantity, the composition or the concentrate type, the required amount of diluting agent, etc. The second code contains at least one piece of information relating to the dialysis solution such as the volume, the composition, the concentrations, etc. of the dialysis solution.

When the concentrate is diluted, the first code is read for this purpose so that the device carrying out the dilution knows the quantity of diluting agent, etc. and can admix a corresponding amount.

Once the dialysis solution has been prepared from the concentrate by dilution, the information of the second code is read so that it is, for example, known, which solution it is.

It is thus possible to carry out both the preparation of the dialysis solution and the administering of the prepared dialysis solution by means of two codes, with the codes preferably containing all the essential information required for the preparation of the dialysis solution and for its administration so that the risk of errors due to an incorrect dilution, to a confusion of solution bags, etc. is minimized.

Provision is preferably made that the first connector and the second connector are releasable from one another, for example by a breakable connection.

The first and second codes are preferably each barcodes. Said barcodes are preferably peripheral so that the orientation of the connector during reading does not play any role.

It is conceivable that a predetermined breaking point is located between the first and second connectors. In this case, the first code is read first and the dialysis solution is then prepared from the concentrate by the admixing of diluting agent, in particular RO water (RO: reverse osmosis). Once this process has been completed, the first connector is broken off and the second connector is plugged into a receiver of a dialysis machine, preferably of a peritoneal dialysis machine, and is read there. The information as to which dialysis solution it is is thus present in the dialysis machine.

Provision is preferably made that the two connectors are arranged behind one another so that the two connectors and thus the two codes can be separated from one another after the preparation of the dialysis solution so that the concentrate container that is encoded by the second code and that contains the dialysis solution is then directly available for the treatment.

The first and second connectors can be connected to one another by a plug-in connector or by a cap connection. It is thus conceivable, for example, that the second connector is plugged onto or into the first connector after the preparation of the dialysis solution. Once the concentrate container having the completed dialysis solution is then connected to the dialysis machine, the second code, and not the first code, is read.

The two connectors are preferably arranged adjacent to one another.

It is conceivable that the first code is arranged spatially further away from the concentrate container than the second code. After the preparation of the dialysis solution, the first code can be separated so that only the second connector remains at the concentrate container and its code can then be read.

The connectors can generally be arranged directly at the concentrate container. It is preferred for the connectors to be arranged at a line piece, in particular at a hose, whose hollow space is in communication with the inner space of the concentrate container. The diluting agent is conducted into the concentrate container and the dialysis solution is also drained from the concentrate container through this line piece.

A line can furthermore be provided that extends between the connector or connectors and the concentrate container, with a connection piece, in particular a Luer connector, being located in the line by which the concentrate container can be separated from the connector or connectors. This makes it possible that the emptied concentrate container can subsequently be used as a drainage container. For this purpose, the connection piece, that can be designed as a plug-in connection, for example, is opened so that the connector is separated from the concentrate container.

The concentrate container, including the connectors having codes, can be provided as a complete unit or can be supplied separately. The possibility of variation for different concentrated ready-made solutions and bag sizes or container sizes is increased by the connection of the individual components of concentrate container and mixing bag without a separate unit (concentrate container and mixing bag) having to be kept in stock for every possible ready-made solution.

A disinfection cap for the connectors can generally be provided to protect against contamination or pollution.

It is conceivable that the concentrate container is rigid. It is, however, generally also covered by the invention that it is a container having flexible walls, i.e. a bag.

A combination of these embodiments is also conceivable and covered by the invention.

It is thus possible that the concentrate container in the sense of the present invention has a plurality of containers, and indeed in the form of a concentrate reception container that contains the concentrate and a solution container for receiving the dialysis solution. Both are in fluid communication with one another so that a solvent, in particular RO water, can first be mixed completely with the concentrate in the concentrate reception container and this mixture, i.e. the dialysis solution, can then be conducted into the solution container. The concentrate reception container has the first connector having the first code and the solution container has the second container having the second code.

The term "concentrate container" can thus not necessarily mean that exactly one container is provided. A plurality of containers can also be provided.

In this respect, the concentrate reception container is preferably designed as a rigid container (cartridge) and/or the solution container is formed as a bag that receives the mixed solution, i.e. the dialysis solution. The fixed wall of the cartridge makes it possible to prevent solvent or undiluted concentrate from being pumped into the dialysis machine since a volume removal is not possible from the fixed container that is not completely filled. In addition, the corresponding suction pressure can be used on the attempt of removal as an indicator for a closure or non-mixing with the empty bag or with the solution container.

The two containers can be connected by means of a connection piece. The concentrate reception container is opened at the bag side or at the side of the solution container due to the connection of the two components.

The form of the inlet or of the outlet opening of the concentrate reception container can support the mixing of the solution with the concentrate.

The concentrate reception container can serve as an air separator.

The solution container, that is preferably designed as a bag, takes over a plurality of functions in a preferred embodiment. With the aid of its closure system it pierces the connector point at the cartridge or at the concentrate reception container; it receives the mixture, i.e. the dialysis solution; it dispenses the dialysis solution during the treatment; and it serves as a drainage bag in the next treatment.

The concentrate reception container is preferably connected to the first connector having the first code and the solution container is connected to the second connector having the second code. In this respect, the two connectors can be on the same side or on different sides of the concentrate reception container. The solution container together with the second connector is preferably releasable from the concentrate reception container, for example in that the second connector is broken off from the concentrate reception container or is separated in another way.

The concentrate container is preferably a disposable article.

It is conceivable that the dialysis machine or the dilution device has a connector strip in which the connector or connectors is/are received and that a rigid concentrate container is mechanically supported by the connector strip. This preferably also applies to the named rigid concentrate reception container.

The present invention furthermore relates to a dialysis machine, in particular to a peritoneal dialysis machine for the carrying out of a dialysis treatment or a peritoneal dialysis treatment, wherein the dialysis machine has at least one receiver for the first connector and/or for the second connector of a concentrate container in accordance with the invention as described herein and reading means for reading the information of the codes located on the connector or connectors, wherein the dialysis machine is configured to dispense diluting agent into the concentrate container and/or to drain the dialysis solution from the container in dependence on the code.

The dialysis machine can have a pump device by means of which the diluting agent, in particular water, is conveyed into the concentrate container. It is conceivable that the dialysis machine is connected to a water supply line and the dialysis solution is prepared by means of the named pump apparatus.

The same dialysis machine or a different dialysis machine, in particular a peritoneal dialysis machine, has reading means for reading the second code so that the dialysis solution is conveyed into the abdomen of the patient by the pump means.

A peritoneal dialysis machine is preferably understood by the term "dialysis machine" within the framework of the present invention. The term or the invention is, however, not restricted to this and also covers other types of dialysis machines. The peritoneal dialysis machine can be one in which the solutions or the diluting agent are conveyed by pumps or in which the flow is effected gravimetrically, i.e. without the use of a pump.

The present invention furthermore relates to a method of preparing a dialysis solution, in particular a peritoneal dialysis solution, wherein a concentrate container in accordance with the invention as described herein is connected to the dialysis machine by the first connector such that the first code is read by the dialysis machine and diluting agent is introduced into the concentrate container in dependence on the first code and such that the first code is subsequently removed or covered and the concentrate container is connected to the same dialysis machine or to a different dialysis machine by the second connector such that the second code is read by the dialysis machine.

It is conceivable that after the dilution of the concentrate the first connector is broken off or is connected to the second connector or is covered by the second connector. The second connector whose code contains information on the dialysis solution that is prepared by the dilution of the concentrate can thus be read.

It is pointed out at this point that the terms "a" and "one" do not necessarily mean that there is exactly one of the elements in question even through this represents a preferred embodiment of the invention. The plural of the elements is rather also covered by the use of these terms. It accordingly applies that the use of a term in the plural also includes the singular and, conversely, the use of a term in the singular also covers the plural of the element in question.

Figure 2:
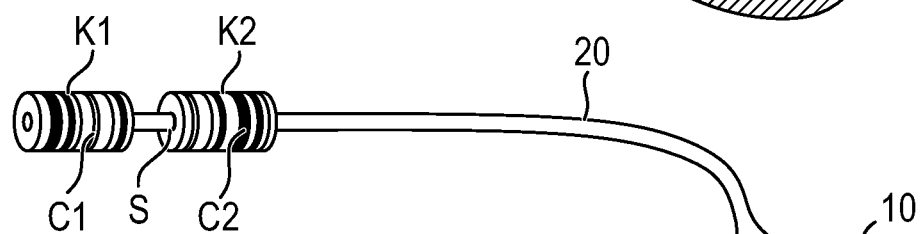
Figure 3:
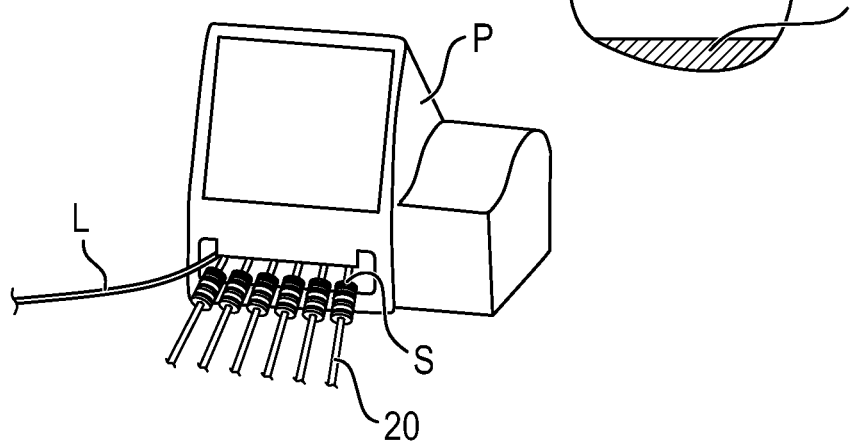
Figure 4:
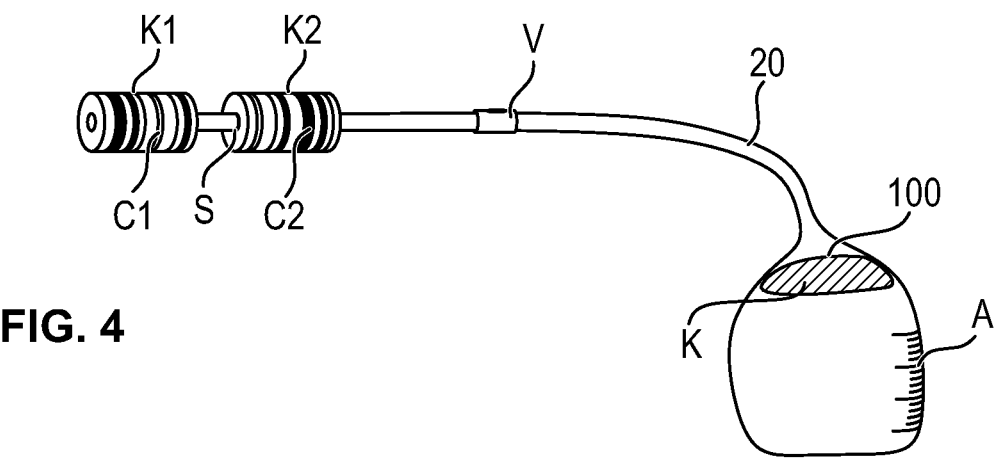

Further details and advantages of the invention will be explained in more detail with reference to an embodiment shown in the drawing. There are shown:

FIG. 1: a concentrate container before the plugging of the second connector to the first connector;

FIG. 2: a concentrate container having two connectors arranged behind one another and a predetermined breaking point therebetween;

FIG. 3: a view of a peritoneal dialysis machine with a plurality of connected bags; and FIG. 4: a concentrate container in accordance with FIG. 2 with a connection piece arranged in the line; and FIG. 5: views of various embodiments of concentrate containers that have a concentrate reception container and a solution container.

It is pointed out that elements that are the same or have the same function are provided with the same numerals in the Figures.

In the embodiment in accordance with FIG. 1, the concentrate container in which a liquid or solid concentrate K is located is shown with the reference numeral 10.

The concentrate container 10 is connected to a hose line 20 at whose end the first connector K1 having a first code C1 is located.

In a dilution station that is formed, for example, by a peritoneal dialysis machine or also by a different unit water is introduced into the interior of the concentrate container 10 through the hose 20 and the concentrate is diluted accordingly. The dilution station reads the first code C1 and carries out the dilution in dependence thereon. After the dilution, the connector strip of the dilution station is opened and the connector or connectors K1 having a connected bag 10 or another concentrate container 10 is/are removed and closed by a cap K2 having a code C2. The code C2 bears information relating to the diluted concentrate, i.e. the dialysis solution.

The codes C1 and C2 are barcodes. A different encoding is also possible, e.g. a different color coding of the connectors.

The bags or concentrate containers encoded in this manner can now be administered to the patient.

The bag connection or the connector is accompanied by a further connector in FIG. 2. In this respect, the connector K2 arranged closer to the concentrate container and having the code C2 is connected by a predetermined breaking point S to the connector K1 arranged further away from the concentrate container and having the code C1.

The connector K2 close to the bag or its code C2 contains information on the diluted concentrate, i.e. on the dialysis solution; the connector K1 remote from the bag or its code C1 contains information on the non-diluted concentrate.

After the dilution of the concentrate K, the connector K1 is broken off so that the concentrate container having the connector K2 is now available for the treatment.

As can be seen from FIG. 3, the peritoneal dialysis machine P in the embodiment shown here serves as a dilution station to provide completed solutions for other peritoneal dialysis machines. The dilution station recognizes the kind of concentrate from the barcode C1 and admixes the required quantity of water.

As can be seen from FIG. 3, a plurality of concentrate containers (six concentrate containers here) can be prepared simultaneously or consecutively by the connection of a plurality of concentrate containers to the same machine.

The patient line L is connected to a solvent supply (e.g. RO water plant) for this purpose. After the first mixing, the bag or the concentrate container is released at the provided breaking point (cf. FIG. 2 and FIG. 3, reference symbol S) and is now immediately available for administering while further mixtures can be prepared.

A conceivable embodiment comprises starting to mix large-volume quantities in order thus to be able to supply a plurality of machines. The set used is no longer available for the treatment after the first mixing of the bags or concentrate containers.

It is furthermore conceivable to add a valve to the connector that only enables the conveying of fluid into the connected bag. An accidental sucking in is thus precluded.

In the embodiment in accordance with FIG. 2, both connectors K1 and K2 are connected to the concentrate container at the start of the filling of the concentrate container, as can be seen from FIG. 2. After the filling of the bag, the connection between the connectors K1 and K2 is released, e.g. by breaking. The concentrate container becomes a clearly identifiably solution bag that contains the dialysis solution by this procedure.

FIG. 4 shows a concentrate container in whose hose line an additional connection piece V is arranged. The concentrate container can thus likewise be used as a drainage bag after the treatment.

A volume specification in the form of scale markings on the bag or concentrate container is marked by reference symbol A. This enables an additional visual check of the filled bags after removal from the filling station, for instance such that the bag has to be filled up to a specific level.

It is conceivable to provide the concentrate container with an additional handle that facilitates its transport, in particular when it is a question of larger amounts of fluid.

The concentrate is present packed in the concentrate container in the embodiment in accordance with FIG. 4. This packaging is marked by reference numeral 100. It degrades on contact with the diluting agent and is preferably located at the inflow of the concentrate container. An optimum intermixing with the solution can thus be achieved during filling.

In a further conceivable embodiment of the invention, the concentrate is dyed with a harmless dye. This enables a check as to whether the concentrate and the diluting agent are sufficiently mixed.

The present invention inter alia provides the advantages named in the following in an advantageous embodiment:

A solution bag or the concentrate container can be removed from the dilution unit directly after completion while the next bags or concentrate containers are being filled.

The solution bags or concentrate containers can be diluted and removed in a time-staggered manner to enable a utilization of the consumption time that is as optimum as possible.

Figure 5A:
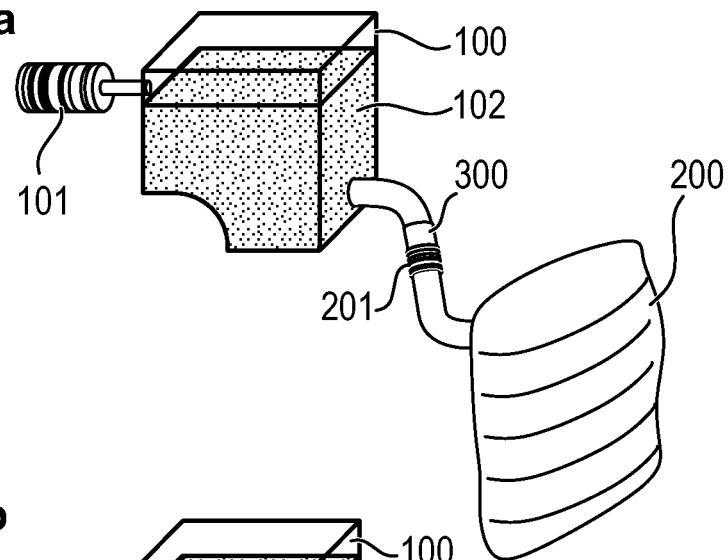

FIG. 5a) shows an embodiment in which the concentrate container has two containers, namely the concentrate reception container 100 having the first connector 101 with the first code, on the one hand, and the solution container 200 having the second connector 201 that is in fluid communication therewith. The concentrate 102 is located in the concentrate reception container 100. Both containers are connected to one another by the connection piece 300. The concentrate reception container 100 is opened toward the bag 200 by this connection.

Figure 5B:
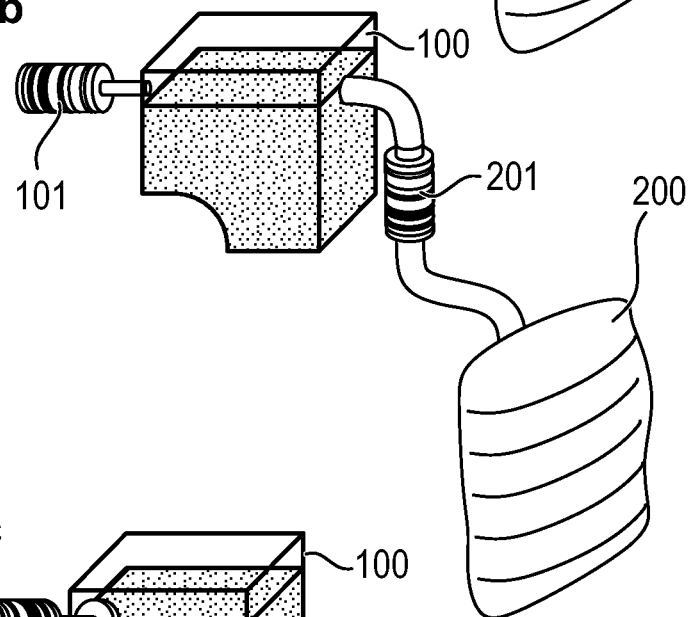

FIG. 5b) shows an embodiment in which the outlet of the concentrate reception container 100 opens in a barcode section or connector 201 to which the bag segment can be connected.

Figure 5C:
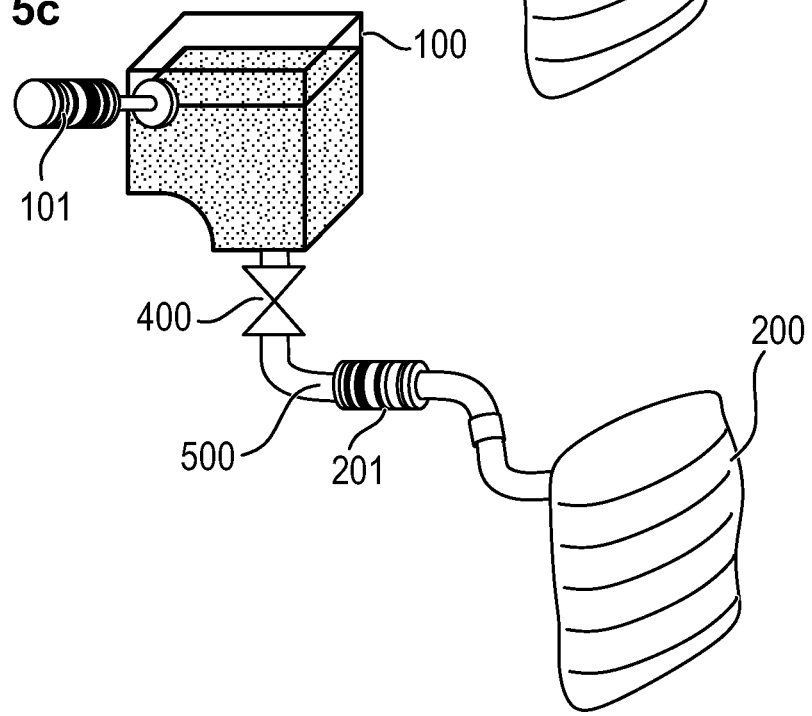

It can be seen from FIG. 5c) that a valve 400 can be provided that enables the conveying of fluid via the cartridge 100 into the connected solution bag 200. The sucking in of the concentrate is thus suppressed from a construction aspect. The connection between the containers is interrupted at 500 after the filling of the solution bag.

A universal empty bag is connected to the cartridge 100 at the start of filling. The connection between the cartridge 100 and the barcode section 201 is released after the filling of the bag. The universal empty bag becomes an unambiguous solution bag that can now be administered using a second cycler by this procedure.

One solution bag can thus be removed from the dilution unit directly after completion while the next bags are being filled. Solution bags can furthermore be diluted and removed in a time-staggered manner to enable a utilization of the consumption time that is as optimum as possible.

Some scenarios are presented in the following that are of an exemplary nature and that do not limit the invention.

Scenario A:

The cycler, i.e. the peritoneal dialysis machine, is connected to a solvent supply in a similar manner to the HD environment; a bag connection (port) of the set is required for this purpose.

The further ports can be occupied by cartridges. The cartridges are connected to the empty bags, typically 6 l.

The treatment procedure can be started directly after the production of the mixture.

Scenario B:

The cycler is connected to a solvent supply. A bag connection (port) of the set is required for this purpose.

Only one port is occupied by the concentrate. The cartridge is connected to a bag that can accept the volume of a complete treatment.

This was previously not possible since the patient does not have to transport this filled bag. Such a procedure reduces the costs and the amount of waste of the disposable article.

Scenario C:

It is equally possible to combine the process with regular solution bags which can be used within the treatment.

Scenario D:

The current patient line is connected to a solvent supply. Up to six bags can thus be started to be mixed in a first step.

In a second step, the initially mixed solution is administered to the patient without changing the set.

Scenario E:

The cycler acts as a dilution station to provide the solutions for other cyclers. It would thus be possible to produce six bags in one mixing procedure.

The current patient line is connected to a solvent supply for this purpose. After the initial mixing, the bag is released from the cartridge and is now available for administering. An advantageous adaptation of the system comprises an initial mixing of large-volume amounts. Since the set used in the mixing unit is not available for a treatment. A cartridge suitable for this purpose can be seen in FIG. 5b.

The invention claimed is:

1. A concentrate container system comprising a concentrate reception container containing a concentrate that is configured to form a dialysis solution after its dilution with a diluting agent, characterized in that the concentrate reception container is linked to a first connector having a first code that contains at least one piece of information on the concentrate and a second connector having a second code different from the first code, with the second code containing at least one piece of information on the dialysis solution, characterized in that first and second connectors are arranged directly at the concentrate reception container or in that the first and second connectors are arranged at a line piece having a hollow space in communication with the inner space of the concentrate reception container.

2. A concentrate container system in accordance with claim 1, characterized in that the first connector and the second connector are releasable from one another.

3. A concentrate container system in accordance with claim 1, characterized in that the first and second codes are each barcodes or color codes.

4. A concentrate container system in accordance with claim 1, characterized in that a predetermined breaking point is located between the first and second connectors.

5. A concentrate container system in accordance with claim 1, characterized in that the first and second connectors are connected to one another by a plug-in connection or a cap connection.

6. A concentrate container system in accordance with claim 1 characterized in that the first code is arranged spatially further away from the concentrate reception container than the second code.

7. A concentrate container system in accordance with claim 1 further comprising a line extending between at least one of the first and second connectors and the concentrate reception container, with a connection piece located in the line by which the concentrate reception container can be separated from the at least one of the first and second connectors.

8. A concentrate container system in accordance with claim 1, characterized in that the concentrate reception container, configured as a single bag, is the only container in the system.

9. A concentrate container system in accordance with claim 1 further comprising a solution container for receiving the dialysis solution.

10. A concentrate container system in accordance with claim 9, characterized in that the concentrate reception container is configured as a rigid container and the solution container is configured as a bag.

11. A concentrate container system in accordance with claim 9, characterized in that the concentrate reception container is linked to the first connector having the first code and the solution container is linked to the second connector having the second code.

12. A dialysis machine, in particular a peritoneal dialysis machine, for the carrying out of a dialysis treatment or a peritoneal dialysis treatment, comprising the concentrate container system in accordance with claim 1, characterized in that the dialysis machine has at least one receiver for the first connector and/or for the second connector of the concentrate container system and reading means for reading the information of the codes located on the connector or connectors, wherein the dialysis machine is configured to dispense diluting agent into the concentrate container and/or to drain the dialysis solution from the concentrate container in dependence on the code.

13. A method of preparing a dialysis solution, in particular a peritoneal dialysis solution, characterized in that the concentrate container system in accordance with claim 1 is connected to a dialysis machine by the first connector such that the first code is read by the dialysis machine and diluting agent is introduced into the concentrate container in dependence on the first code and such that the first connector is subsequently removed or covered or is connected to the second connector and the concentrate container is connected to the same dialysis machine or to a different dialysis machine by the second connector such that the second code is read by the dialysis machine.

14. A method in accordance with claim 13, characterized in that after the dilution of the concentrate the first connector is broken off or is connected to the second connector or is covered by the second connector.

* * * * *